US011932973B2

(12) United States Patent
Chou et al.

(10) Patent No.: US 11,932,973 B2
(45) Date of Patent: Mar. 19, 2024

(54) METHOD FOR MANUFACTURING A POLYMER-BASED FIBROUS SCAFFOLD (71) Applicant: Academia Sinica, Taipei (TW)

(72) Inventors: Chia-Fu Chou, Taipei (TW); Balchandar Navaneethan, Taipei (TW)

(73) Assignee: ACADEMIA SINICA, Taipei (TW)

(*) Notice: Subject to any disclaimer, the term of this patent is extended or adjusted under 35 U.S.C. 154(b) by 220 days.

(21) Appl. No.: 17/511,641

(22) Filed: Oct. 27, 2021

(65) Prior Publication Data
US 2022/0136145 A1 May 5, 2022

Related U.S. Application Data (60) Provisional application No. 63/108,898, filed on Nov. 3, 2020.

(51) Int. Cl.
D03D 27/00 (2006.01)
D01D 5/00 (2006.01)

(52) U.S. Cl.
CPC ............ D03D 27/00 (2013.01); D01D 5/003 (2013.01); D10B 2331/041 (2013.01)

(58) Field of Classification Search
CPC .................. D01D 5/003; D01B 2331/041
USPC .................................................. 264/437
See application file for complete search history.

(56) References Cited

U.S. PATENT DOCUMENTS

2014/0207248 A1   7/2014   Wang et al.

FOREIGN PATENT DOCUMENTS

| CN | 102582293 A | 7/2012 |
| CN | 105350089 A | 2/2016 |
| CN | 105882036 A | 8/2016 |
| CN | 107718531 A | 2/2018 |
| CN | 111676537 A | 9/2020 |
| TW | 201016909 A | 5/2010 |

OTHER PUBLICATIONS

Balchandar Navaneethan, Gnaneshwar Puvala Vijayakumar, Laiva Ashang Luwang, Stalin Karuppiah, Venugopal Jayarama Reddy, Seeram Ramakrishna, and Chia-Fu Chou, Novel Self-Directing Single-Polymer Jet Developing Layered-Like 3D Buckled Microfibrous Scaffolds for Tissue Engineering Applications, ACS Appl. Mater. Interfaces 2021, 13, 9691-9701.

Primary Examiner — Jeffrey M Wollschlager
Assistant Examiner — Xue H Liu
(74) Attorney, Agent, or Firm — BACON & THOMAS, PLLC (57) ABSTRACT A method for manufacturing a polymer-based fibrous scaffold is disclosed. The method includes the following step: providing an electrospinning device comprising a collector; and injecting a polymer solution into the electrospinning device to produce a single jet fiber, wherein the single jet fiber is piled on the collector to form a fibrous scaffold.

13 Claims, 12 Drawing Sheets

METHOD FOR MANUFACTURING A POLYMER-BASED FIBROUS SCAFFOLD

CROSS REFERENCE TO RELATED APPLICATION

This application claims the benefit of filing date of U.S. Provisional Application Ser. No. 63/108,898, entitled "REPRODUCIBLE AND TUNABLE ELECTROSPUN 3D POROUS BUCKLED-PCL MICROFIBROUS SCAFFOLDS DEVELOPED BY SELF-DIRECTING SINGLE POLYMER JET" filed Nov. 3, 2020 under 35 USC § 119(e)(1).

BACKGROUND OF THE INVENTION

1. Field of the Invention

The present disclosure relates to a method for manufacturing a polymer-based fibrous scaffold, more particularly, a method for manufacturing the fibrous scaffold by an electrospinning device producing a single jet fiber to manufacture the fibrous scaffold.

2. Description of Related Art

With the advancement of technology and the development of an aging society, various biomedical materials have also been continuously improved. Bio-scaffold can be used to replace partially damaged tissues or organs to restore the function and appearance of damaged tissues, thereby solving difficulties in organ transplantation or high rejection rate. Bio-scaffolds are considered a material with potential because they can reduce the risk of thrombosis.

Electrospinning is a technique for bio-scaffold fabrication. However, in the conventional electrospinning process, the polymer jet ejected from the needle tip is divided into plural jet fibers, and the fibers deposit on the collector in a random motion under a high-voltage electric field, resulting in poor controllability over scaffold morphology, which is unfavorable to manufacture a three-dimensional fibrous scaffold. In addition, the bio-scaffolds manufactured by the conventional electrospinning have disadvantages such as poor mechanical strength or poor cellular infiltration ability.

Therefore, it is desirable to provide a method for manufacturing a fibrous scaffold to improve the disadvantages of conventional technology.

SUMMARY OF THE INVENTION

In view of this, the present disclosure provides a method for manufacturing a fibrous scaffold to improve the disadvantages of conventional technology, such as poor distinguishability, poor reproducibility, poor mechanical strength, or poor cellular infiltration ability pertained of the fibrous scaffold.

To achieve the aforementioned goal, the present disclosure provides a method for manufacturing a polymer-based fibrous scaffold, comprising the following steps: providing an electrospinning device comprising a collector; and injecting a polymer solution into the electrospinning device to produce a single jet fiber, wherein the single jet fiber is piled to form a fibrous scaffold on the collector.

In the present disclosure, the single jet fiber is piled on the collector by auto-switching between the two modes of a whipping motion and a cantilever-like single jet, respectively, thereby manufacturing an improved fibrous scaffold.

Specifically, the single jet fiber may be piled at a first direction by the whipping motion, and the first direction is perpendicular to the surface of the collector. Therefore, the single jet fiber may be piled on the collector in multiple layers. In addition, the single jet fiber may be piled at a second direction and a third direction by the cantilever-like single jet, and the second direction and the third direction are respectively perpendicular to the first direction. Therefore, the single jet fiber is piled in a spiral shape.

In the conventional electrospinning processing, a plurality of jet fibers is generated by applying a high voltage to a polymer solution with low viscosity. However, the plurality of jet fibers deposit on a collector in a random motion, resulting in poor controllability over scaffold morphology. In the present disclosure, a single jet fiber is generating and the single jet fiber is piled on a collector by auto-switching between the two modes of a whipping motion and a cantilever-like single jet, thereby manufacturing fibrous scaffolds with similar shape, area or thickness; therefore, the reproducibility of the fibrous scaffold is improved.

Generally, a tightly packed thin film is formed because fiber deposition is a continuous process. In the present disclosure, the continuous fibers piled during the whipping motion can be temporarily transitioned by the cantilever-like single jet. Therefore, the single jet fiber of the present disclosure forms a fibrous scaffold being multi-layered like and separable after the single jet fiber is deposited by auto-switching between the two modes of a whipping motion and a cantilever-like single jet, thereby providing more room to accommodate a greater number of cells. Accordingly, it improves the culture condition for the cells in a three-dimensional fibrous scaffold.

The present disclosure does not impose any particular limitation on the method for generating a single jet fiber. For example, a suitable polymer, or a suitable concentration or viscosity of a polymer solution can be selected. In the present disclosure, the suitable polymer comprises polycaprolactone (PCL), polyglycolide (PGA), polylactic acid (PLA), polytetrafluoroethylene (PTFE), Polyacrylonitrile (PAN), polyvinyl chloride (PVC), polyurethane, poly(methyl methacrylate) (PMMA), polyether, polycarbonate, copolymer thereof or a combination thereof. However, the present disclosure is not limited thereto. In the present disclosure, the suitable concentration of the polymer solution may be in a range from 5% to 30%, for example, from 10% to 20%, greater than 15% to 30%, greater than 15% to 25%, or greater than 15% to 20%. However, the present disclosure is not limited thereto. In the present disclosure, the suitable viscosity of the polymer solution may be in a range from 50 cP to 2000 cP, for example, from 200 cP to 420 cP. However, the present disclosure is not limited thereto.

In the present disclosure, the polymer solution comprises at least one organic solvent. A suitable organic solvent comprises chloroform, diethyl ether, tetrahydrofuran, dimethylacetamide, ethanol, propanol, isopropanol, butanol, isobutanol, tert-butanol, cyclobutanol, hexafluoro isopropanol (HFIP), or a combination thereof. However, the present disclosure is not limited thereto.

In the fibrous scaffold manufactured by the present disclosure, the average diameter of the fiber may be in a range from 1 μm to 100 μm, for example, it may be in a range from 1 μm to 80 μm, 1 μm to 60 μm, 1 μm to 40 μm, 1 μm to 20 μm, 1 μm to 10 μm, or 5 μm to 10 μm, but the present disclosure is not limited thereto. The average diameter of the fiber can be adjusted by the viscosity of the polymer solution, the boiling point of the solvent used, or the voltage applied in electrospinning. In addition, in the present disclosure, the fibers in the fibrous scaffold may have a rough surface, which can increase the friction between the fibers and the cells, thereby promoting cell adhesion. More specifically, the surface of the fibers in the fibrous scaffold may comprise a plurality of pores, which can provide spaces to cells to improve the cell attachment of the fibrous scaffold.

In the fibrous scaffold manufactured by the present disclosure, the fiber packing density may gradually reduce from the base layer to the top layer. Therefore, the fibrous scaffold of the present disclosure may have a gradient porous structure (GPS), which can promote angiogenesis and accelerate the formation of blood vessels, thereby promoting the healing of chronic wounds.

The pore size of the conventional fibrous scaffold is inversely proportional to the mechanical strength of the fibrous scaffold. In other words, the increase in the pore size of the fibrous scaffold will reduce the mechanical strength of the fibrous scaffold. However, in the present disclosure, since the fibrous scaffold has a gradient fiber packing density, a fibrous scaffold with structural resiliency may be provided; and, the mechanical strength of the fibrous scaffold can be improved. In the present disclosure, the pore size of the fiber of the fibrous scaffold may be in a range from 3 μm to 100 μm, for example, it may be in a range from 3 μm to 80 μm, 5 μm to 80 μm, 5 μm to 70 μm, 5 μm to 50 μm, or 5 μm to 40 μm. However, the present disclosure is not limited thereto.

In the fibrous scaffold manufactured by the present disclosure, the fiber of the fibrous scaffold may comprise a plurality of fiber segments and a capsule morphology segment, the capsule morphology segment is located between two of the adjacent plurality of fiber segments, and the diameter of the capsule morphology segment is greater than that of the two of the adjacent plurality of fiber segments. For example, the diameter of the capsule morphology segment is about 1.1 to 2 times the diameter of the fiber segment.

In addition, a fibrous scaffold with improved pattern writing accuracy, improved pattern resolution, or improved replication efficiency can be obtained by the single fiber jet piling up through auto-switching between the two modes of a whipping motion and a cantilever-like single jet; and, it has potential in application.

In the present disclosure, the collector may be a conducting template, and the type or shape of the collector is not particularly limited, for example, it may be a flat collector, a grid collector, or a three-dimensional collector. In one aspect of the present disclosure, the collector may be a three-dimensional collector, so the formed fibrous scaffold may be a three-dimensional fibrous scaffold, preserving the topographic fidelity of the collector; and, the three-dimensional fibrous scaffold may have improved reliability or cell adhesion.

Herein, the "auto-switching" refers that the charge retention or dissipation on the single jet fiber causing a rapid switching between the two modes of a whipping motion and a cantilever-like single jet. The term "base layer" used herein refers to the side of the fibrous support adjacent to the collector in a cross-sectional view. The term "top layer" used herein refers to the side of the fibrous support away from the collector in a cross-sectional view.

In summary, the present disclosure provides a novel method for manufacturing a polymer-based fibrous scaffold through the production of single jet fibers. The manufactured fibrous scaffold may have improved resolution, reproducibility, or mechanical strength.

Other objects, advantages, and novel features of the invention will become more apparent from the following detailed description when taken in conjunction with the accompanying drawings.

DETAILED DESCRIPTION OF THE PREFERRED EMBODIMENT

The implementation of the present disclosure is illustrated by specific embodiments to enable persons skilled in the art to easily understand the other advantages and effects of the present disclosure by referring to the disclosure contained therein. The present disclosure is implemented or applied by other different, specific embodiments. Various modifications and changes can be made in accordance with different viewpoints and applications to details disclosed herein without departing from the spirit of the present disclosure.

In the present disclosure, unless otherwise specified, comprising or having "one" or "an" element is not limited to having a single element, while one or more elements may be provided. In addition, ordinal numbers such as "first" and "second" used in the specification and claim for modifying elements of the claim do not mean and represent the claimed elements have any antecedent ordinal number, nor do they represent the order (or order of production) between a claimed element and another claimed element. The ordinal numbers are only intended to distinguish a component with a name from another component with the same name.

In the present disclosure, the terms such as "comprise", "include", "contain", and "have" are open-ended words, so they should be interpreted as "contain but not limited to". Therefore, when the terms "comprise", "include", "contain", and/or "have" are used in the description of the present disclosure, they specify the existence of corresponding features, regions, steps, operations and/or components, but do not exclude one or more the existence of corresponding features, regions, steps, operations and/or components.

In the present disclosure, the terms "range from the first value to the second value" or "in a range from the first value to the second value" means the said range comprises the first value the second value and other values between them.

EXPERIMENT METHOD

Embodiment

Polycaprolactone (mw 80,000 kD) (PCL) was dissolved in a mixed solvent of chloroform/diethyl ether (volume ratio of 9:1) and hexafluoroisopropanol (HFIP) to prepare 15.78% polymer solution. A 5 mL syringe of an electro spinning device was filled with the polymer solution, which was attached with a 22G blunt needle, the syringe was loaded in a syringe pump, and a positive voltage probe was connected to a needle tip. The syringe pump was set to dispense the solution at 3 mL/hr. rate, and a 10-kV voltage was supplied to the needle to electrospin the polymer solution. The produced single jet fibers were collected on a collector, and the collector was placed at 14 cm distance from the needle tip.

Comparative Example

Polycaprolactone (mw 80,000 kD) (PCL) was dissolved in a mixed solvent of chloroform/diethyl ether (volume ratio of 9:1) and hexafluoroisopropanol (HFIP) to prepare 10% or 15% polymer solution. A 5 mL syringe of an electrospinning device was filled with the polymer solution, which was attached with a 22G blunt needle, the syringe was loaded in a syringe pump, and a positive voltage probe was connected to a needle tip. The syringe pump was set to dispense the solution at 3 mL/hr. rate, and a 10-kV voltage was supplied to the needle to electrospin the polymer solution. The produced multi jet fibers were collected on a collector, and the collector was placed at 10 cm distance from the needle tip.

Analysis of Fiber Preparation Process

Figure 1A:
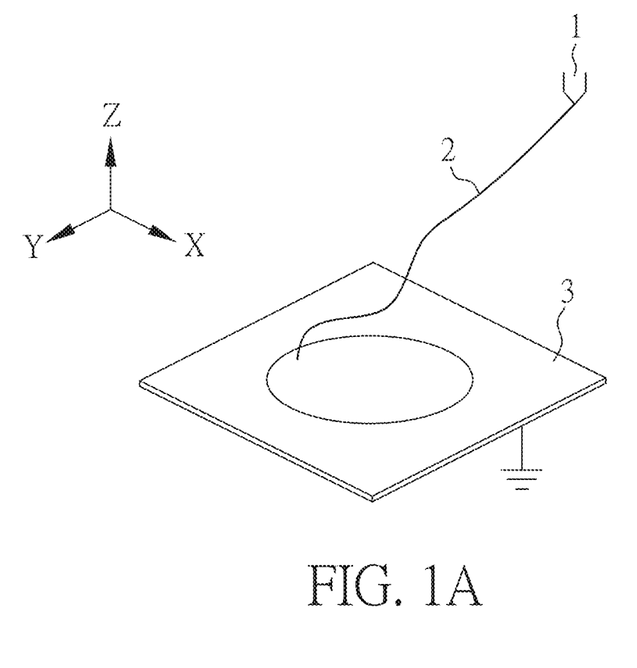
FIGS. 1A and 1B are schematic diagrams of the method for manufacturing the polymer-based fibrous scaffold according to the present disclosure.
Figure 1B:
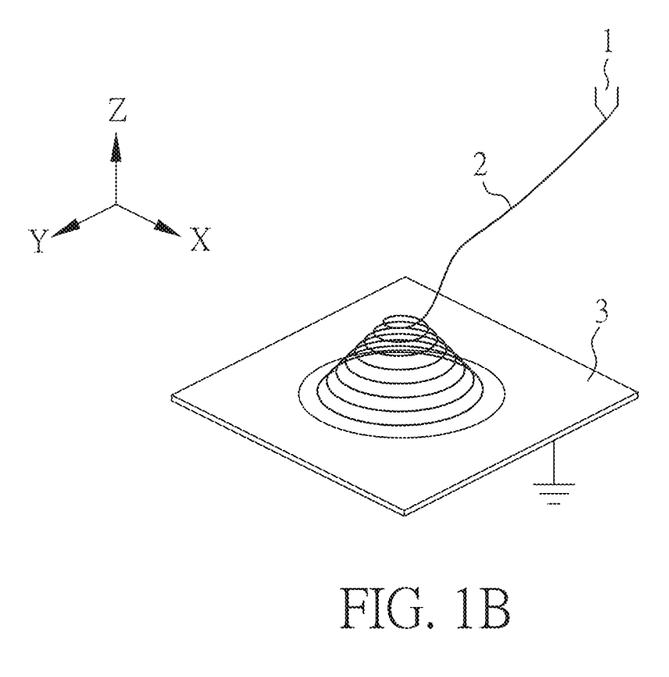
Figure 2:
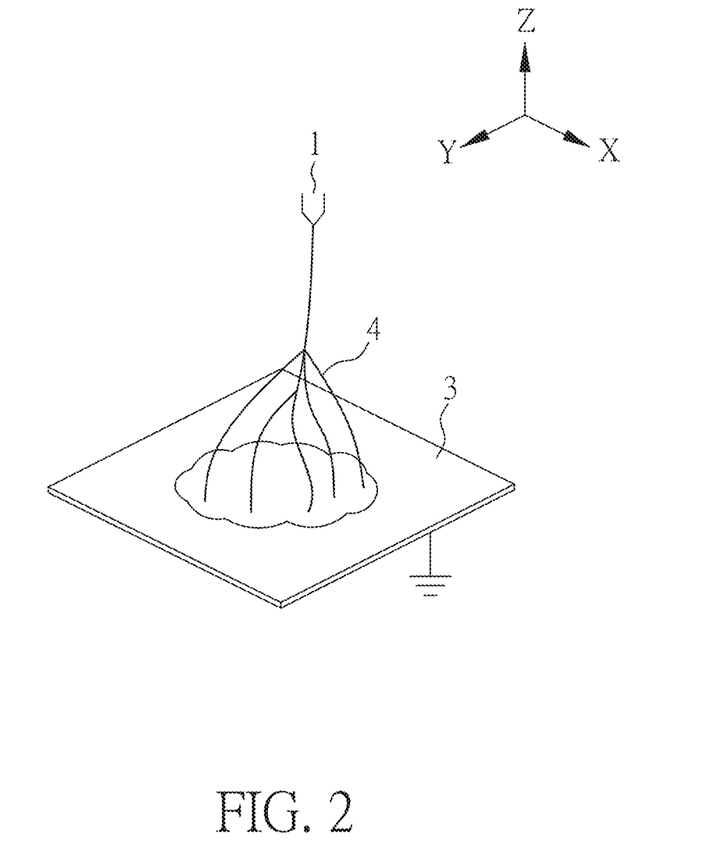
FIG. 2 is a schematic diagram of a method for manufacturing a polymer-based fibrous scaffold according to a comparative example.

The electrospinning processes of embodiment and comparative example were recorded using a high-speed camera (Phantom Miro 3, Vision Research, NJ, USA), they were recorded at 1000 frames per second, and FIG. 1A to FIG. 2 showed the results. FIGS. 1A and 1B are schematic diagrams of the method for manufacturing the polymer-based fibrous scaffold according to the present disclosure. FIG. 2 was a schematic diagram of a method for manufacturing a polymer-based fibrous scaffold according to a comparative example. In addition, for the convenience of description, part of the detailed structure of the electrospinning device was omitted.

In the preparation method of the present disclosure, as shown in FIG. 1A, the electrospinning device 1 generates a single jet fiber 2 which deposited at a first direction Z through a whipping motion, and the first direction Z was vertical to the surface of the collector 3. Furthermore, as shown in FIG. 1B, the single jet fiber 2 was piled at a second direction X and a third direction Y by the cantilever-like single jet, and the second direction X and the third direction Y are respectively perpendicular to the first direction Z. In addition, it was observed from high-speed camera records that the single jet fiber 2 was able to auto-switch between the whipping motion shown in FIG. 1A and the cantilever-like single jet shown in FIG. 1B to pile the single jet fiber 2 on the collector 3 on. Therefore, the single jet fiber 2 was able to pile on the collector 3 in a spiral shape, and pile up in multiple layers at the first direction Z.

On the contrary, when the electrospinning of comparative example was performed under the same conditions as embodiment, it was observed from the records of the high-speed camera (as shown in FIG. 2) that the electrospinning device 1 produced multi jet fibers 4 rather than the single jet fiber described in the present disclosure; and, the multi jet fibers 4 were deposited on the collector 3 in a random motion.

After repeating the above experiment 6 times, it was found that the fibrous scaffold prepared by the preparation method of the present disclosure would obtain similar shape, size and weight over all the 6 experiments, which proved that the present disclosure could improve the reproducibility of the fibrous scaffold. However, the multi jet fibers of the comparative example were deposited in a random motion, so that they exhibited poor reproducibility.

Fiber Morphology

Figure 3:
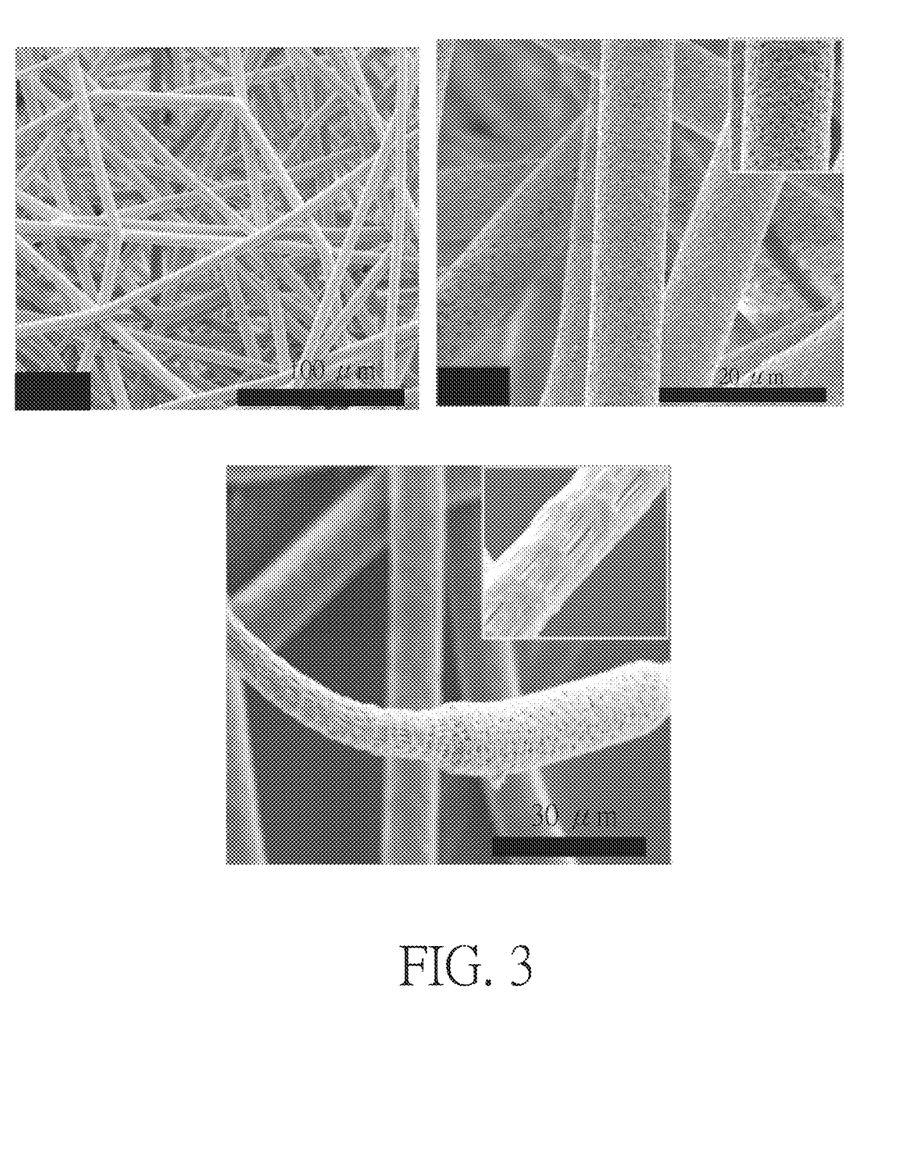
FIG. 3 is an SEM image of a polymer-based fibrous scaffold according to an embodiment of the present disclosure.
Figure 4:
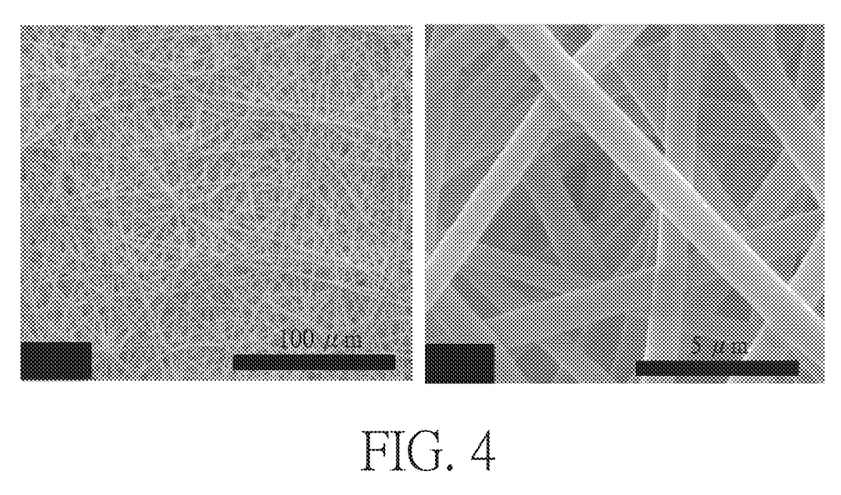
FIG. 4 is an SEM image of a polymer-based fibrous scaffold according to a comparative example.

As shown in FIG. 3 and FIG. 4, fiber morphology was studied using scanning electron microscopy (SEM) (FEI company Inspect F, USA) at an accelerating voltage of 5 kV and 10 kV, after coating the fiber surface with gold by an automatic sputter coater (JEOLJFC-1200 Fine Coater, Japan). ImageJ software (NIH, USA) was used for measuring the fiber diameter. The surface roughness was investigated using a 3D confocal laser scanning microscope (Keyence VK-X 1000, USA). FIG. 3 was an SEM image of a polymer-based fibrous scaffold according to an embodiment of the present disclosure. FIG. 4 was an SEM image of a polymer-based fibrous scaffold according to a comparative example.

The fiber diameter of the embodiment was about 8.64±0.49 µm, which had a larger fiber diameter than the comparative example (0.812±0.15 µm). As shown in FIG. 3, the fiber surface of the embodiment had a plurality of pores, and the maximum penetration depth of field (DOF) and the average surface height were 248.08 µm and 37.09 µm, respectively. In addition, it was also observed that the fiber of the embodiment had a cylindrical capsule morphology; in more detail, the fiber of the embodiment had a plurality of fiber segments and a capsule morphology segment, the capsule morphology segment was located between two of the adjacent plurality of fiber segments, and the diameter of the capsule morphology segment was greater than that of the two of the adjacent plurality of fiber segments. This capsule morphology was generated as a result of extensive jet stretching at each bending point while traveling in a helical direction. However, the fiber surface of the comparative example was not observed to have the characteristics of multiple holes or the cylindrical capsule morphology. Compared with the fiber of the embodiment, the fiber of the comparative example had a smoother surface, as shown in FIG. 4, and the maximum penetration DOF and average surface height were 22.89 μm and 2.374 μm, respectively. Therefore, the fiber surface of the embodiment was a rough surface, and had a higher roughness than the comparative example.

Figure 5A:
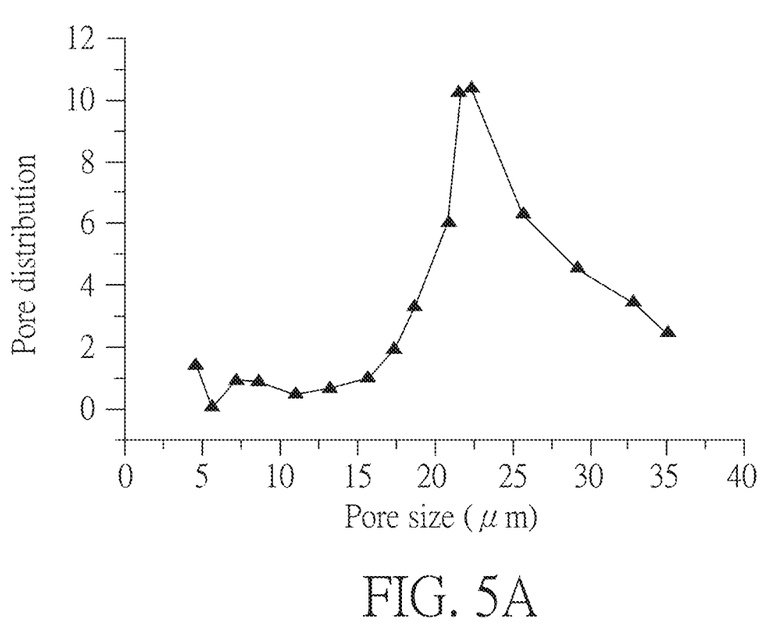
FIG. 5A is a diagram showing the pore size distribution of a polymer-based fibrous scaffold according to an embodiment of the present disclosure.
Figure 5B:
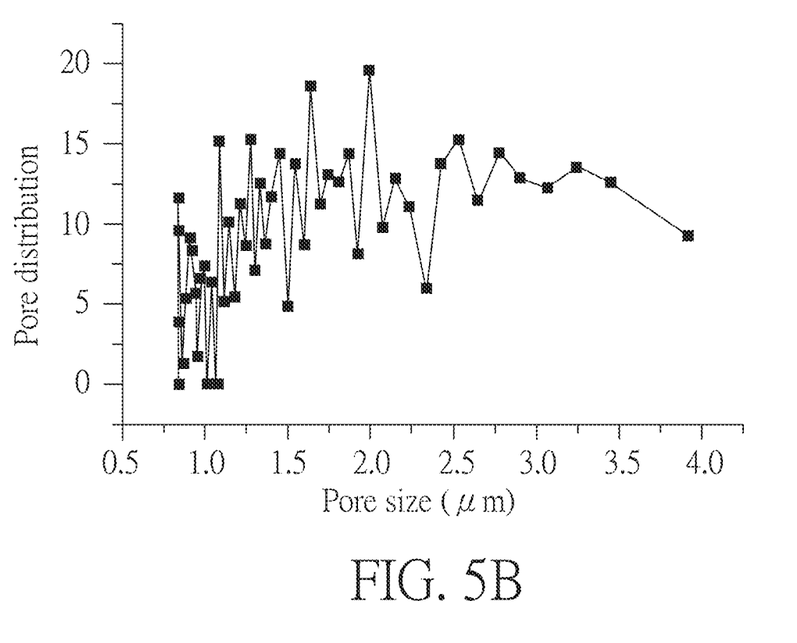
FIG. 5B is a pore size distribution diagram of a polymer-based fibrous scaffold of a comparative example.
Figure 6A:
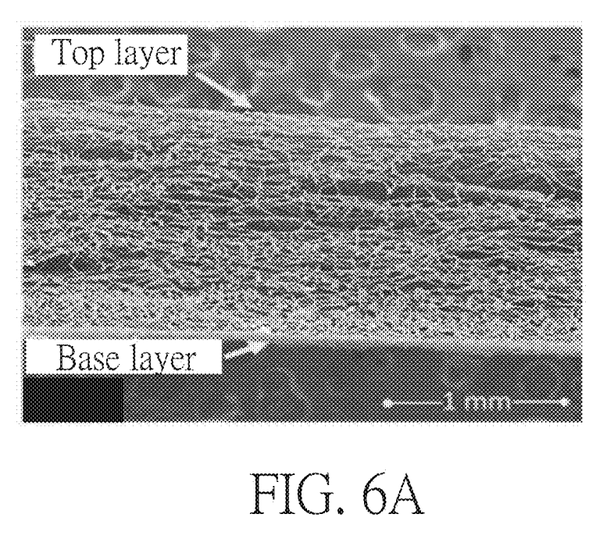
FIG. 6A is an SEM image of a cross-section of a polymer-based fibrous scaffold according to an embodiment of the present disclosure.
Figure 6B:
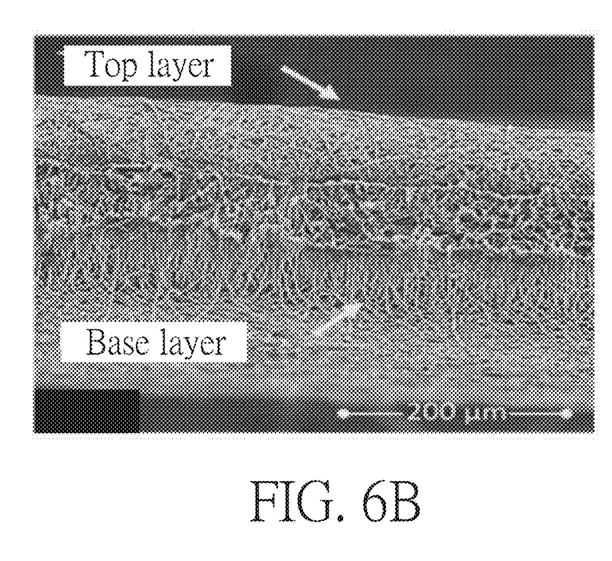
FIG. 6B is an SEM image of a cross section of the polymer-based fibrous scaffold of a comparative example.

The pore size of the scaffolds was determined using the capillary flow porometer (CFP-1200-A, Ithaca, NY, USA), as shown in FIG. 5A and FIG. 5B. The fibrous scaffolds of embodiment and comparative example were immersed in liquid nitrogen, then they were cut into two halves and subjected to SEM imaging, as shown in FIG. 6A and FIG. 6B. FIG. 5A was a diagram showing the pore size distribution of a polymer-based fibrous scaffold according to an embodiment of the present disclosure. FIG. 5B was a pore size distribution diagram of a polymer-based fibrous scaffold of a comparative example. FIG. 6A was an SEM image of a cross-section of a polymer-based fibrous scaffold according to an embodiment of the present disclosure. FIG. 6B was an SEM image of a cross section of the polymer-based fibrous scaffold of a comparative example.

As shown in FIG. 5A and FIG. 6A, the pore size of the fibrous scaffold of the embodiment ranged from about 5 μm to 35 μm, and the fiber packing density gradually reduced from the base layer to the top layer. Therefore, the fibrous scaffold of the present disclosure had a gradient porous structure. In addition, a sponge-like structural characteristic resulted from the different fiber packing density, thereby providing structural resiliency to the fibrous scaffold. Herein, the term "base layer" refers to the side of the fibrous support adjacent to the collector in a cross-sectional view. The term "base layer" used herein refers to the side of the fibrous support away from the collector in a cross-sectional view. On the contrary, as shown in FIG. 5B and FIG. 6B, the pore size of the fibrous scaffold of the comparative example ranged about from 0.8 μm to 4 μm and had a narrower pore size distribution, and the formed fibrous scaffold was a tightly packed thin film.

Mechanical Strength of the Fiber

Figure 7:
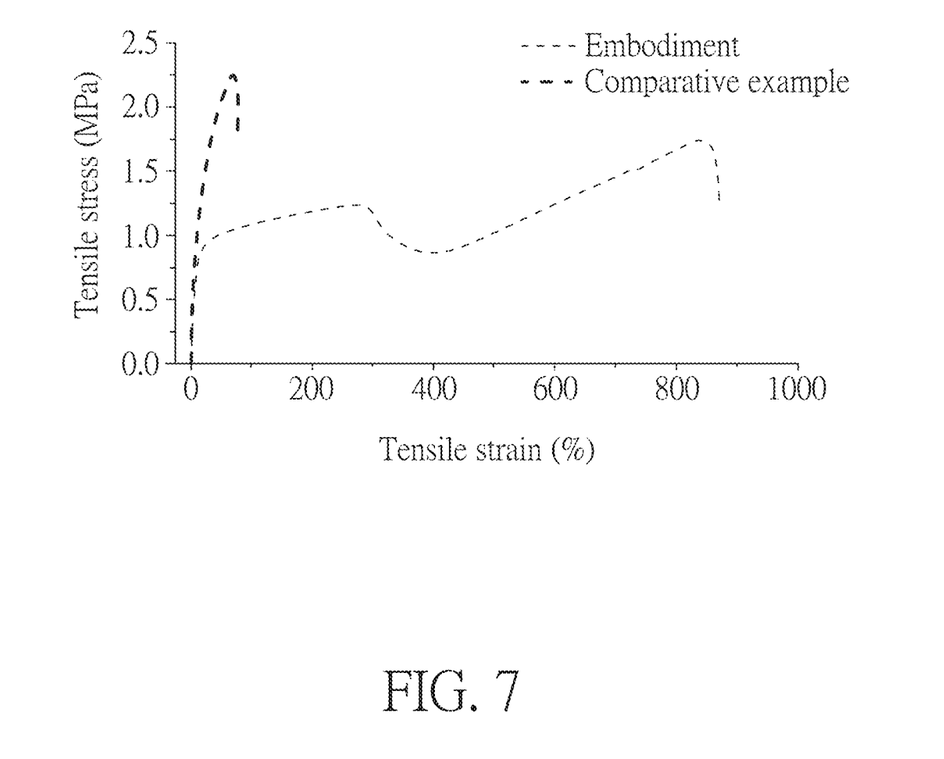
FIG. 7 shows a tensile stress-strain curve of the polymer-based fibrous scaffolds of an embodiment of the present disclosure and a comparative example.

Tensile strength of the scaffolds was studied using a tabletop tensile tester (Instron 3345, USA). The tensile stress-strain curve was recorded with the tensile tester software (Blue Hill Materials Testing Software, Instron, USA), as shown in FIG. 7.

Generally, the increase in the pore size of the fibrous scaffold will reduce the mechanical strength of the fibrous scaffold. However, as shown in FIG. 7, the fibrous scaffold of the embodiment exhibited an ultimate tensile stress of 1.75 MPa at high strain value of 850%. The fibrous scaffold of the embodiment was able to withstand greater deformation before rupture, compared with the fibrous scaffold of comparative example exhibiting an ultimate tensile stress of 2.25 MPa at strain value of 80%. Accordingly, the fibrous scaffold of the embodiment has better mechanical strength, and the mechanical strength was about 10 times higher than that of the comparative example.

Pattern Writing Precision

Figure 8A:
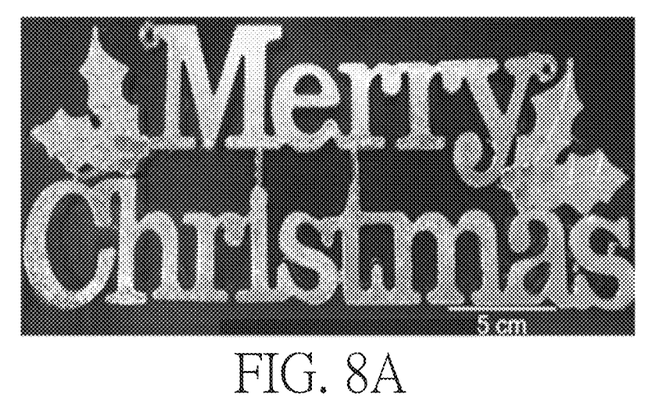
FIG. 8A to FIG. 8C are images comparing the pattern writing accuracy of the polymer-based fibrous stents of an embodiment of the present disclosure and a comparative example.
Figure 8B:
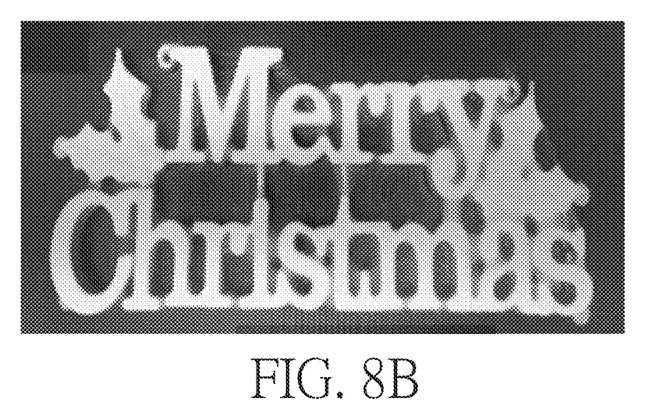
Figure 8C:
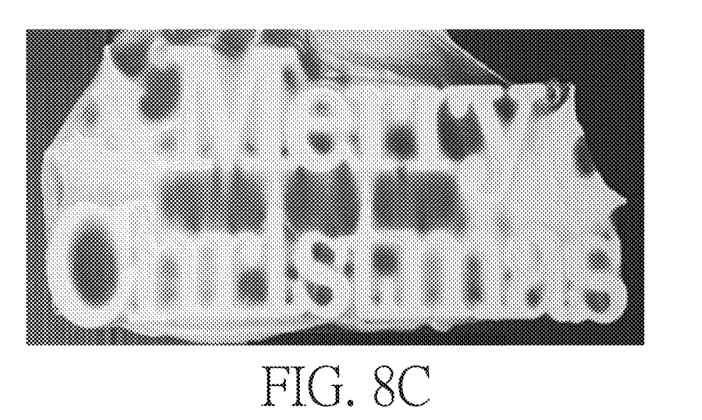

The pattern writing precisions of the method used in the embodiment and comparative example were compared by direct deposition of fibers on a conducting template collector having the shape of "Merry Christmas", as shown in FIG. 8A to FIG. 8C. FIG. 8A was an image of the conducting template. FIG. 8B was an image showing the pattern writing of the fibrous scaffold of the embodiment. FIG. 8C was an image showing the pattern writing of the fibrous scaffold of the comparative example.

As shown in FIG. 8B, the pattern developed by the fibrous scaffold of embodiment appeared identical to the template, and it demonstrated that the embodiment had excellent ability of pattern writing. On the contrary, the fibrous scaffold of the comparative example covered the gaps between the structure and showed poor ability of pattern writing. Therefore, it was found that the pattern writing precision of the fibrous scaffold of the embodiment was better that that of comparative example.

Pattern Writing Resolution

Figure 9A:
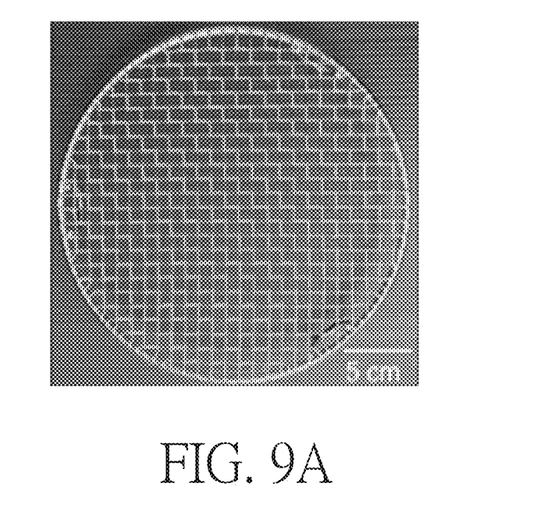
FIG. 9A to FIG. 9C are images comparing the pattern writing resolution of the polymer-based fibrous stents of an embodiment of the present disclosure and a comparative example.
Figure 9B:
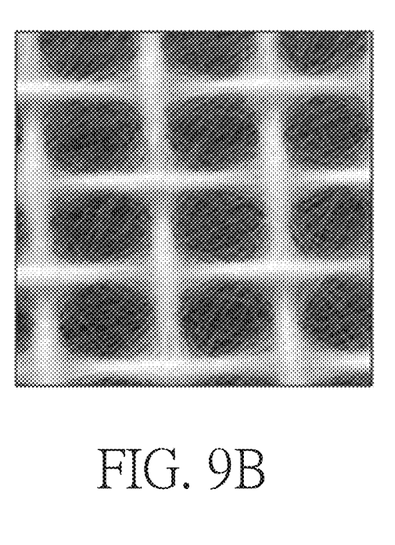
Figure 9C:
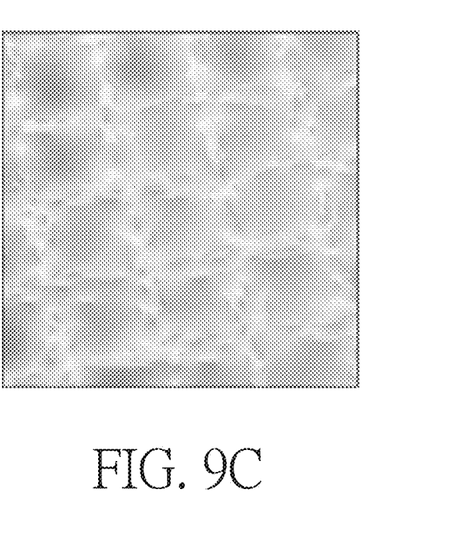

As shown in FIG. 9A to FIG. 9C, a metal grid rack was used as collector to study the pattern writing resolutions of the embodiment and comparative example, and fibers were directly piled on the metal grid racks by using the method of embodiment and comparative example, respectively. FIG. 9A was an image of the metal grid rack. FIG. 9B was an image of the pattern writing resolution of the fibrous scaffold of embodiment. FIG. 9C was an image of the pattern writing resolution of the fibrous scaffold of comparative example.

As shown in FIG. 9B, the single jet fibers generated from the embodiment could deposit along the metal grid rack shown in FIG. 9A without any external control or tuning, and thus only a small number of fibers connected to each other between the gaps of the metal grid rack. On the contrary, as shown in FIG. 9C, the multi jet fibers generated from the comparative example deposited on the metal gird rack randomly, such that the fibers covered the gaps between the grid lines, and it showed poor pattern writing resolution. As a result, the pattern writing resolution of the embodiment was better than that of comparative example.

Writing Ability for a Three-Dimensional Template-1

Figure 10A:
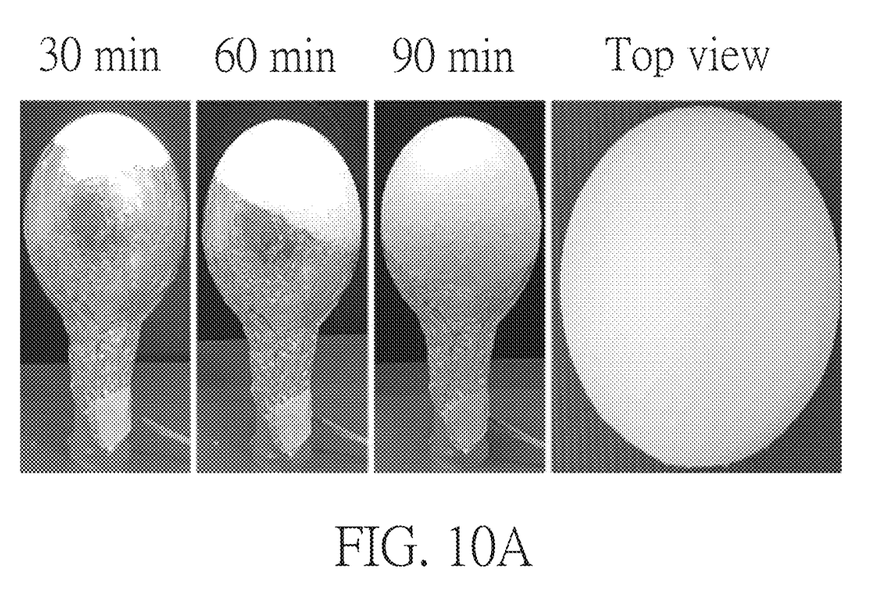
FIG. 10A is an image of a single jet fiber of an embodiment piled on a 3D collector over time of the present disclosure.
Figure 10B:
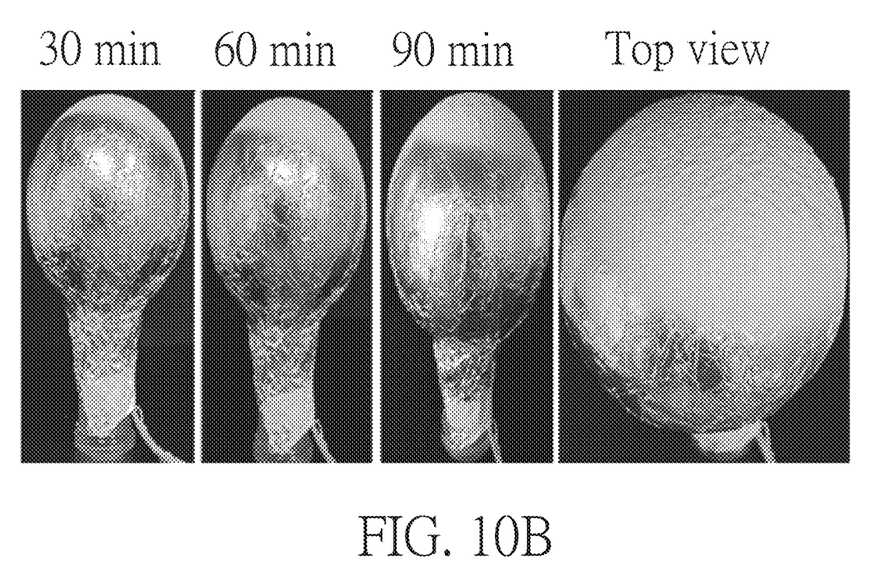
FIG. 10B is an image of multi jet fibers of a comparative example piled up on the 3D collector over time.

An upside-down positioned round bottom flask wrapped by aluminum foil was used as a collector, the fiber of embodiment and comparative example were directly deposited on the 3D template, respectively; and, their writing abilities were compared, as shown in FIG. 10A and FIG. 10B. In addition, FIG. 10A was an image of a single jet fiber of an embodiment piled on the 3D collector over time. FIG. 10B was an image of multi jet fibers of a comparative example piled up on the 3D collector over time.

As shown in FIG. 10A, the single jet fiber of the embodiment increased the fiber deposition area and thickness uniformly in circular shape through whipping motion and cantilever-like single jet, thus covering all sides of the sphere from upside to downside with time. In addition, the fibrous scaffold of the embodiment could be easily removed from the collector and put back to the collector, while maintaining its structure and shape. On the contrary, the multi jet fibers of fibrous scaffold of the comparative example deposited randomly and it deposited at the same site during the deposition process, and thus failing to achieve the complete replication for the template, as shown in FIG. 10B.

Writing Ability for a Three-Dimensional Template-2

Figure 11A:
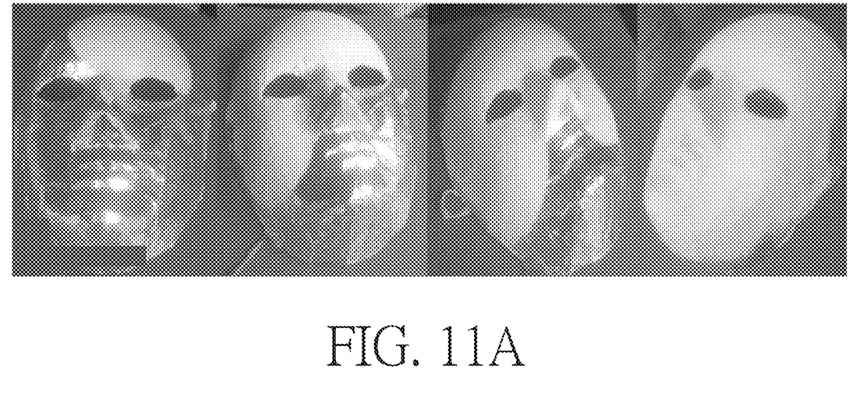
FIG. 11A is an image of a single jet fiber piled up on a 3D human face mask over time according to an embodiment of the present disclosure.
Figure 11B:
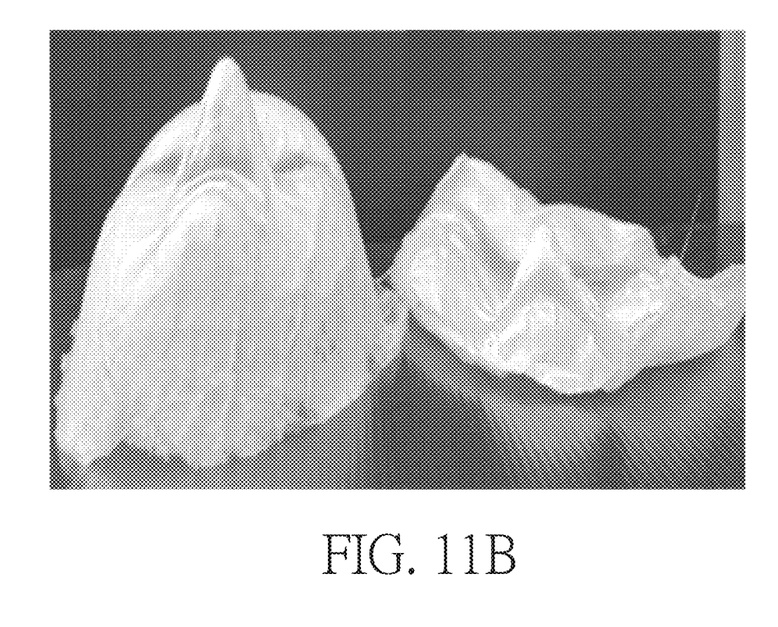
FIG. 11B is an image comparing the fibrous scaffold of a 3D human face mask of an embodiment of the present disclosure with a 3D human face mask of a comparative example.

A 3D human face mask was used as a collector, the fiber of the embodiment and the fiber of comparative example were directly deposited on the 3D human face mask, respectively; and, the possibility of replicating a 3D fibrous scaffold having irregular shape was studied, as shown in FIG. 11A and FIG. 11B. In addition, FIG. 11A was an image of a single jet fiber piled up on a 3D face mask over time according to an embodiment. FIG. 11B was an image comparing the fibrous scaffold of a 3D human face mask of an embodiment with a 3D human face mask of a comparative example.

As shown in FIG. 11A, the single jet fiber of the embodiment increased the fiber deposition area and thickness uniformly, thus covering all sides of the 3D human face mask template from upside to downside with time. In addition, as shown in left part of FIG. 11B, the fibrous scaffold of the embodiment stayed in a three-dimensional shape without extra support after removing the 3D human face mask template. On the contrary, the multi jet fiber of the comparative example failed to achieve the complete replication for the 3D human face mask template, and it collapsed after removing the 3D human face mask template, thus failing to stay in a three-dimensional shape, as shown in the right part of FIG. 11B.

Figure 12:
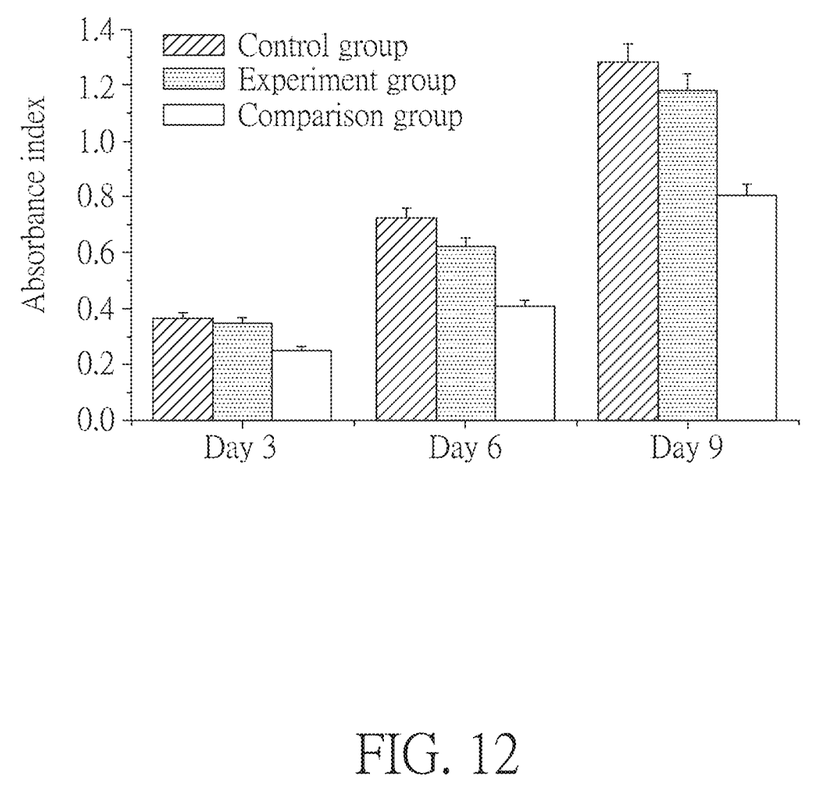
FIG. 12 shows the cell proliferation results of the 3D fibrous scaffolds of an embodiment and a comparative example of the present disclosure.

Scaffolding Properties of the 3D Fibrous Scaffold Mimicking Extracellular Matrix The mouse embryonic fibroblast (3T3) cells (ATCC, USA) were cultured in Dulbecco's Modified Eagle's Medium (DMEM) supplemented with 10% (v/v) fetal bovine serum, 100 unit/mL of penicillin and 100 mg/mL of streptomycin in the humidified incubator at 37° C. with 5% $CO_2$ in a tissue culture flask. Once the cultured cells reached their confluency, cells were trypsinized followed by centrifugation. The cell pellet was resuspended in 2 ml of culture medium, then the cells were counted using trypan blue assay with the use of hemocytometer; and, $1 \times 10^4$ cells per well were seeded over the scaffolds in 24 well plates and placed in an incubator to facilitate the cell growth on the fibrous scaffolds. Cell viability was quantified using MTS reagent on day 3, 6, and 9 over control group, experiment group, and comparison group, observed at the absorbance range of 490 nm with a spectrometric plate reader, as shown in FIG. 12. In addition, the control group used a standard tissue culture plate as a fibrous scaffold; the experiment group used a fibrous scaffold from the embodiment; and the comparison group used the fibrous scaffold from the comparative example.

As shown in FIG. 12, it was observed that the fibrous scaffold of the embodiment has rougher surface and porous fiber morphology, thereby providing better cell-fiber attachment and proliferation rate, compared with the comparative example. In addition, the fibrous scaffold of the embodiment had improved cellular infiltration, thereby enhancing the survival and proliferation rate. On the contrary, the fibrous scaffold of the comparative example had relative smooth surface would cause the cells to slide off easily from the seeding site during the initial cell attachment, affecting the cellular attachment. In addition, the fibrous scaffold of the comparative example had poor cellular infiltration, affecting the cell survival and proliferation rate. According to the experimental results, the cell density on the fibrous scaffold of the experiment group increased by 21% and 38%, respectively, compared with the comparison group on day 6 and day 9.

In addition, it was found from the SEM analysis that the cellular infiltration ability was improved to make the cells infiltrate into the inner layers of the fibrous scaffold of the embodiment, because the fibrous scaffold of the embodiment had a multi-layered construction being separable, more specifically, the 3D porous structure of the fibrous scaffold of the embodiment had more open and interconnected pores.

Therefore, the fibrous scaffold of the present disclosure could provide more room to accommodate a greater number of cells, and the cells form 3D networks through the interaction therebetween, and thus it had potential in tissue engineering applications.

Although the present invention has been explained in relation to its preferred embodiment, it is to be understood that many other possible modifications and variations can be made without departing from the spirit and scope of the invention as hereinafter claimed.

What is claimed is:

1. A method for manufacturing a polymer-based fibrous scaffold, comprising the following steps:
   providing an electro spinning device comprising a collector; and
   injecting a polymer solution into the electrospinning device to produce a single jet fiber, wherein the single jet fiber is piled to form the polymer-based fibrous scaffold on the collector,
   wherein a fiber packing density of the polymer-based fibrous scaffold is gradually reduced from a base layer of the polymer-based fibrous scaffold to a top layer of the polymer-based fibrous scaffold.

2. The method of claim 1, wherein the single jet fiber is piled on the collector by auto-switching between two modes of a whipping motion and a cantilever-like single jet, respectively.

3. The method of claim 2, wherein the single jet fiber is piled at a first direction by the whipping motion, and the first direction is perpendicular to a surface of the collector.

4. The method of claim 3, wherein the single jet fiber is piled at a second direction and a third direction by the cantilever-like single jet, and the second direction and the third direction are respectively perpendicular to the first direction.

5. The method of claim 1, wherein the single jet fiber is piled in a spiral shape.

6. The method of claim 1, wherein the single jet fiber is piled on the collector in multiple layers.

7. The method of claim 1, wherein the polymer-based fibrous scaffold is a three-dimensional fibrous scaffold.

8. The method of claim 1, wherein a surface of a fiber of the polymer-based fibrous scaffold comprises a plurality of pores.

9. The method of claim 1, wherein the polymer solution comprises at least one organic solvent.

10. The method of claim 1, wherein the collector is a three-dimensional collector.

11. The method of claim 1, wherein an average diameter of a fiber of the polymer-based fibrous scaffold is in a range from 1 μm to 100 μm.

12. The method of claim 1, wherein a size of a pore of a fiber of the polymer-based fibrous scaffold is in a range from 3 μn to 100 μm.

13. The method of claim 1, wherein a fiber of the polymer-based fibrous scaffold comprises a plurality of fiber segments and a capsule morphology segment, the capsule morphology segment is located between two of the adjacent plurality of fiber segments, and a diameter of the capsule morphology segment is greater than that of the two of the adjacent plurality of fiber segments.

\* \* \* \* \*